(12) United States Patent
Fischer et al.

(10) Patent No.: US 9,216,051 B2
(45) Date of Patent: Dec. 22, 2015

(54) ELECTROSURGICAL ASSEMBLY AND ELECTROSURGICAL INSTRUMENT

(75) Inventors: Klaus Fischer, Nagold (DE); Alexander Neugebauer, Moessingen (DE); Matthias Voigtlaender, Gomaringen (DE); Daniel Schaeller, Tuebingen (DE); Mara Szyrach, Tuebingen (DE); Joerg Kronenthaler, Hirrlingen (DE); Lars Blobel, Ammerbuch-Entringen (DE); Irina Sigle, Moessingen (DE); Markus D. Enderle, Tuebingen (DE)

(73) Assignee: ERBE ELEKTROMEDIZIN GMBH (DE)

( * ) Notice: Subject to any disclaimer, the term of this patent is extended or adjusted under 35 U.S.C. 154(b) by 493 days.

(21) Appl. No.: 13/576,246

(22) PCT Filed: Dec. 15, 2010

(86) PCT No.: PCT/EP2010/069755
§ 371 (c)(1),
(2), (4) Date: Jul. 31, 2012

(87) PCT Pub. No.: WO2011/095253
PCT Pub. Date: Aug. 11, 2011

(65) Prior Publication Data
US 2012/0303016 A1  Nov. 29, 2012

(30) Foreign Application Priority Data

Feb. 4, 2010 (DE) .......... 10 2010 000 305
Mar. 10, 2010 (DE) .......... 10 2010 015 899

(51) Int. Cl.
*A61B 18/04* (2006.01)
*A61B 18/12* (2006.01)
*A61B 18/00* (2006.01)

(52) U.S. Cl.
CPC ... *A61B 18/1206* (2013.01); *A61B 2018/00011* (2013.01); *A61B 2018/00017* (2013.01); *A61B 2218/008* (2013.01)

(58) Field of Classification Search
CPC ........ A61B 18/00; A61B 18/02; A61B 18/04;
A61B 18/06; A61B 18/08; A61B 18/10;
A61B 18/12; A61B 18/14; A61B 18/18;
A61B 18/20; A61B 18/22; A61B 18/24;
A61N 1/10; A61N 5/00; A61N 5/06; A61M 5/19; A61M 5/20
See application file for complete search history.

(56) References Cited

U.S. PATENT DOCUMENTS

| | | | |
|---|---|---|---|
| 5,613,966 | A | 3/1997 | Makower et al. |
| 5,707,402 | A | 1/1998 | Heim |

(Continued)

FOREIGN PATENT DOCUMENTS

| | | |
|---|---|---|
| CA | 2426003 | 5/2002 |
| CN | 1188629 A | 7/1998 |

(Continued)

OTHER PUBLICATIONS

Japanese Office Action for JP 2012-551521, Dated Mar. 1, 2014, English translation attached to original, All together 8 Pages.

(Continued)

*Primary Examiner* — Theodore Stigell
*Assistant Examiner* — Elizabeth K So
(74) *Attorney, Agent, or Firm* — Brooks Kushman P.C.

(57) ABSTRACT

An electrosurgical assembly is disclosed having an electrosurgical instrument, a detection device for detecting a predetermined constituent of the atmosphere in the region of a treatment site and a treatment unit, which can be connected to the instrument and a current generator for providing RF energy. The treatment unit includes a mechanism for influencing the treatment process depending on an output signal of the detection device.

7 Claims, 12 Drawing Sheets

(56) References Cited

U.S. PATENT DOCUMENTS

Figure 1:
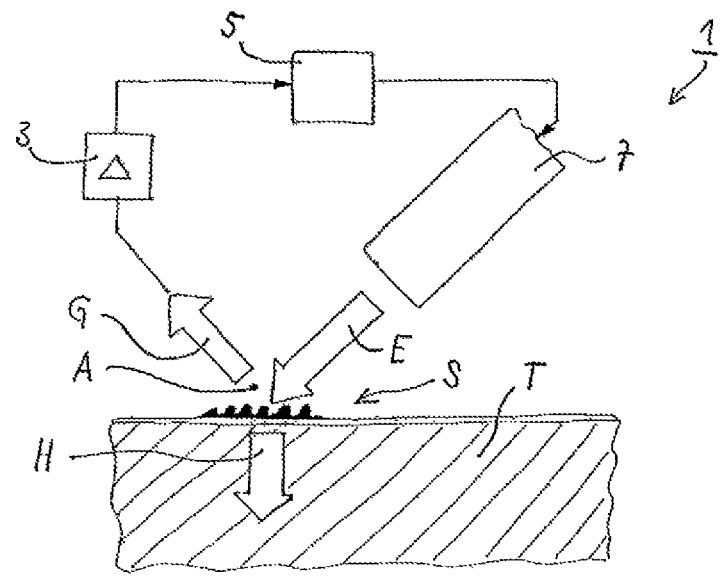

| | | |
|---|---|---|
| 5,725,524 A | 3/1998 | Mulier et al. |
| 5,945,924 A | 8/1999 | Marman et al. |
| 7,749,217 B2 | 7/2010 | Podhajsky |
| 2004/0260281 A1 | 12/2004 | Baxter, III et al. |
| 2005/0199784 A1 | 9/2005 | Jaffar et al. |
| 2006/0025760 A1 | 2/2006 | Podhajsky |
| 2006/0069387 A1 | 3/2006 | Gedebou |
| 2007/0135779 A1 | 6/2007 | Lalomia et al. |
| 2008/0146890 A1 | 6/2008 | LeBoeuf et al. |
| 2008/0319441 A1 | 12/2008 | Seid |
| 2009/0024122 A1 | 1/2009 | Fischer |
| 2009/0149851 A1 | 6/2009 | Craig |
| 2009/0187187 A1 | 7/2009 | Asirvatham et al. |
| 2009/0235720 A1 | 9/2009 | Smith |
| 2014/0012155 A1 | 1/2014 | Flaherty et al. |

FOREIGN PATENT DOCUMENTS

| | | |
|---|---|---|
| CN | 1242095 A | 1/2000 |
| CN | 1473024 | 2/2004 |
| CN | 1667480 A | 9/2005 |
| CN | 1681447 | 10/2005 |
| CN | 101449143 A | 6/2009 |
| DE | 69530493 | 3/2004 |
| DE | 102005021304 | 11/2006 |
| DE | 60315970 | 5/2008 |
| EP | 0779794 | 4/2003 |
| EP | 1501435 | 8/2007 |
| GB | 2456533 | 7/2009 |
| JP | 06178780 | 6/1994 |
| JP | 2001501485 | 2/2001 |
| WO | 9308897 A1 | 5/1993 |
| WO | 9635383 | 11/1996 |

OTHER PUBLICATIONS

Russian Office Action for Russian Application No. 2012134273, English Translation attached to original, Dated Feb. 14, 2014, All together 7 Pages.

International Search Report for PCT/EP2010/069755, English Translation attached to original, Both Completed by the European Patent Office on Feb. 18, 2011, All together 7 Pages.

ELECTROSURGICAL ASSEMBLY AND ELECTROSURGICAL INSTRUMENT

CROSS-REFERENCE TO RELATED APPLICATION

This application is a U.S. national phase of PCT Appln. No. PCT/EP2010/069755, now published WO 2011/095253, filed on Dec. 15, 2010, which claims priority to German Patent Application No. 10 2010 000 305.0 filed on Feb. 4, 2010 and German Patent Application No. 10 2010 015 899.2 filed on Mar. 10, 2010, the disclosures of which are incorporated in their entirety by reference herein.

DESCRIPTION

The invention relates to an electrosurgical assembly, which comprises an electrosurgical instrument and a treatment unit, which can be connected to said instrument, for providing the energy required for a surgical intervention, specifically RF energy. It also relates to an electrosurgical instrument and to a treatment unit of such an assembly. Hereafter, the term "treatment unit" should be understood in a more general sense than that of a conventional RF generator; this will be discussed in more detail further below.

Electrosurgical assemblies of this type are known per se and have long been in clinical use and in some cases even ambulatory use. Many patent publications of the applicant are concerned with their improvement from various aspects. When such assemblies are used, emissions occur, especially fumes, consisting of a large number of different organic molecules. It is known to remove these fumes from the atmosphere above the treatment site by special extraction devices, in order to prevent adverse effects on the surgeon's work due to deterioration of the viewing conditions.

A reduction of the carbonization causing the development of fumes is already performed by APC technology; argon-assisted cutting in electrosurgery is also a first measure for keeping carbonization as low as possible.

Fume analysis before explosion-critical electrosurgical applications takes the approach of reducing the probability of the formation of an explosive gas mixture to a low level. This is achieved by denying food to the patient undergoing the endoscopic examination prior to the operation and performing thorough cleaning of the intestine by means of flushing before the colonoscopy is performed.

Furthermore, fume analysis may be used to reduce the probability of a fire in the intestines or transbronchial system. To avoid fire in the tracheobronchial system when using APC, the oxygen concentration must lie below 40%. Fume analysis is also suitable for reducing tissue carbonization and carcinogenic constituents that form on the tissue surface and can be found in the fume. Finally, the surgeon's view of the operating area is improved, in particular in closed lumina.

The invention is based on the object of providing an improved assembly of the generic type that makes it possible in particular for the cutting or treating process to be influenced more selectively, while at the same time largely preventing emission-induced adverse effects on the surgeon's work.

This object is achieved from a system aspect by an electrosurgical assembly with the features of claim 1 and from the aspect of individual system components by an electrosurgical instrument with the features of claim 13 and a treatment unit with the features of claim 15.

The invention is based on the underlying idea that the emissions occurring in the case of an electrosurgical process have a composition that is characteristic of the conduction of the process. Furthermore, the invention involves the idea of using this available information instead of removing the information-bearing emissions from the treatment site unused—as was previously the practice. This happens by providing a detection device for analyzing the emissions (fumes). Finally, the invention involves the idea of using the analysis results for controlling the surgical process and providing corresponding means in the treatment unit. The treatment unit may in principle be controlled manually, taking the analysis result into account, but direct control by an output signal of the detection device is preferred.

The analysis of these fumes or aerosols opens up the following possibilities:

a. Carbonization is an unwanted side-effect of virtually all electrosurgical applications. Carbonization leads to increased inflammation of the tissue and an increased number of post-operative problems. Therefore, reducing the carbonization in electrosurgical applications (RF and APC applications) is desirable. It is possible for this to be realized by determining combustion-relevant chemical substances of the fume and feeding back the measurement signal for controlling the treatment unit. The extent of the carbonization can also be significantly reduced by supplying specific gaseous or liquid substances (oxidizing agents for the carbon occurring).

b. In the case of electrosurgical applications, under certain conditions there is the risk of a gas explosion, deflagration or fire. Analysis of the gas atmosphere at the operating site or analysis of the fume in the case of electrosurgical applications can be effectively used to prevent explosion, deflagration or fire by releasing the RF energy only when there is a non-explosive gas mixture. An example of this is the prevention of a colonic explosion by the analysis and evaluation of the combustible gases present in the colon, methane and hydrogen. A further application possibility is that of urology, with respect to an APC application under water, in which considerable amounts of hydrogen are formed.

c. The vaporization of biological tissue is a desirable effect in the area of tumour removal and in other areas in which biological tissue is intended to be removed entirely. Vaporization is established in the area of laser application. In electrosurgery too, combustion of biological tissue that is selective, locally resolved and as stoichiometric as possible is intended to achieve selective vaporization of tissue. Vaporization is intended to be used primarily for the removal of tumour tissue.

The selective and locally resolved application of an oxidizing agent (for example oxygen) is necessary for this.

d. Fumes may consist of a large number of different organic molecules, tumour markers, metabolites, DNA, membrane molecules, peptides, proteins and viruses. Analysis of the fume allows the analysis of marker molecules, which for example allow a tissue differentiation to be performed. Healthy tissue can thus be differentiated from diseased (for example tumourous) tissue or a depth effect can be detected by detection of specific substances in the wall structure of mucous membranes (stomach, esophagus, intestine). This results in increased certainty with respect to undesirable instances of damage at depth and perforation.

Measuring principles of the sensors may be of a chemical, electrochemical, spectroscopic, physical or physical-chemical nature. Examples of this are measured value acquisition by fuel cells, paramagnetism, electrochemical measuring cells, pellistors, piezoelectric components, electrical resistance, absorption of radiation, moisture, light, thermal radiation, material composition of an environment, distance, elongation, through-flow, color, magnetic field or pH.

The sensors with associated sensor line may be integrated in the surgical instrument or externally attached to it and, in particular, be protected from the ingress of harmful substances by a semipermeable membrane at the distal end of the surgical instrument.

One embodiment of the invention provides that at least part of the detection device is arranged in a distal region of the electrosurgical instrument. As an alternative to this, it may be provided that at least part of the detection device is arranged in a proximal region of the electrosurgical instrument or away from the instrument and the instrument has a first fluid channel for passing gas through to the detection device.

A further preferred embodiment of the invention provides that the detection device has a fume detector, in particular an $H_2$ or $CH_4$ detector or marker molecule detector. The actual embodiment of the detector may revert to the sensor principles mentioned further above, compact and low-cost commercially available detectors being preferred in particular.

A further refinement of the invention provides that the detection device has means for depositing and an analysis device for analyzing aerosol or solid particles transported with the gas. This allows additional information that is not used directly and necessarily for controlling the surgical process in progress to be made available in the sense mentioned above for tissue differentiation and tumour detection. Parts of the detection device may in this case also be arranged away from the treatment site and from the instrument that is in use, for instance in an analysis laboratory, and are nevertheless understood in the present case as a component of the electrosurgical assembly.

A further refinement of the invention provides that the detection device has a sensor for sensing a physical variable at the treatment site, in particular the temperature, or an optical variable, and/or a distance sensor for sensing a distance between the distal end of the electrosurgical instrument and a tissue to be treated. Here, too, there is a link with the aforementioned sensor principles, and one which goes beyond the detection of chemical compounds in the atmosphere at the treatment site. For example, in a further channel there may be provided an optical waveguide, which allows an optical measurement signal to be analyzed outside the endoscopic instrument, for example with the aid of UV-Vis spectroscopy.

In a further embodiment of the invention, the means for influencing the treatment process have a fluid source for providing a treatment fluid suitable for influencing the treatment process, in particular an oxygen or noble-gas cylinder or a water tank for receiving water or an aqueous solution, and the electrosurgical instrument has a second fluid channel for passing the treatment fluid for influencing the treatment process through to the distal end of the instrument.

In particular, the surgical instrument may additionally have one or more openings, which allow the extraction or introduction of gaseous or liquid substances laterally and/or frontally. This makes it possible for example to introduce a suitable liquid or gaseous oxidizing agent, such as water or oxygen, for reducing the carbonization (see further above), which leads to a better post-operative healing process. Likewise, the substance introduced can bring about a cooling effect, which has a bearing on the tissue effect. These openings may have various embodiments, for example be round, oval or half-round. The openings at the distal end of the probe may be shaped such that an aerosol of a substance applied in liquid form can be produced and applied to the biological tissue in the region of the electrosurgical application.

It may also be provided that a first conveying device for conveying gas in the distal-proximal direction and/or a second conveying device for conveying a treatment fluid for influencing the treatment process in the proximal-distal direction is/are provided in the electrosurgical instrument or in fluid connection with it. The mentioned second conveying device is particularly used for supplying a treatment fluid that is not provided in a pressure vessel, such as for instance when supplying a saline solution from a corresponding tank.

Both when using a pressurized treatment fluid and when providing a conveying device for the treatment fluid, flow control means for controlling the amount of treatment fluid suitable for influencing the treatment process that is supplied to the treatment site per unit of time are preferably provided. These flow control means act in the sense of the means mentioned further above for influencing the treatment process, either on their own or together with means for controlling the supply of treatment energy, specifically RF energy. As such means, the assembly preferably comprises a control device of the power generator that is connected in signaling terms to the output of the detection device, in particular an on/off control and/or power output control.

In a further embodiment of the invention, the aforementioned second fluid channel is arranged within an electrosurgical electrode of the instrument. For example, through such a supply line an input of oxygen or the input of a mixture of oxygen with other gaseous substances can take place with a suitable flow, which has the sustained effect of vaporization of biological tissue. The sensor can detect the concentration of combustion-relevant molecules, and the vaporization of the tissue is maximized and the carbonization minimized by regulating the generator power output and/or the gas flow. In this way, tumour ablation by way of APC or RF technology would be conceivable.

The features that can be assigned to the aforementioned embodiments of the instrument, in particular the first and/or second fluid channel and/or an integrated detection device, at the same time characterize the electrosurgical instrument as a relatively independent unit or product, in the same way as the features that can be assigned to the treatment unit characterize that unit as an independent unit.

Figure 2A:
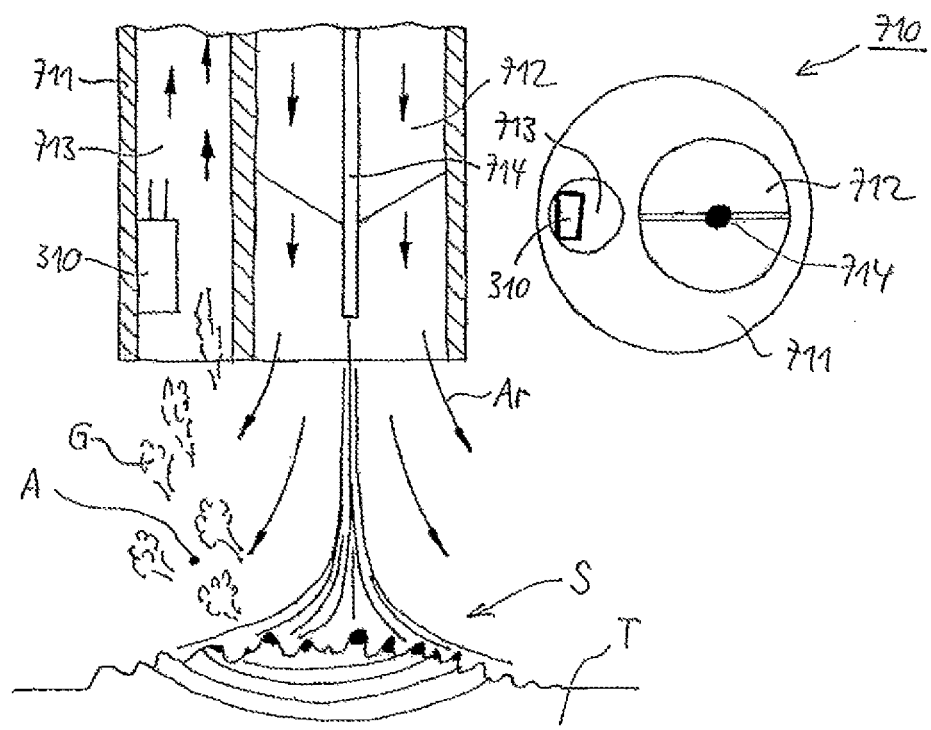
Figure 2B:
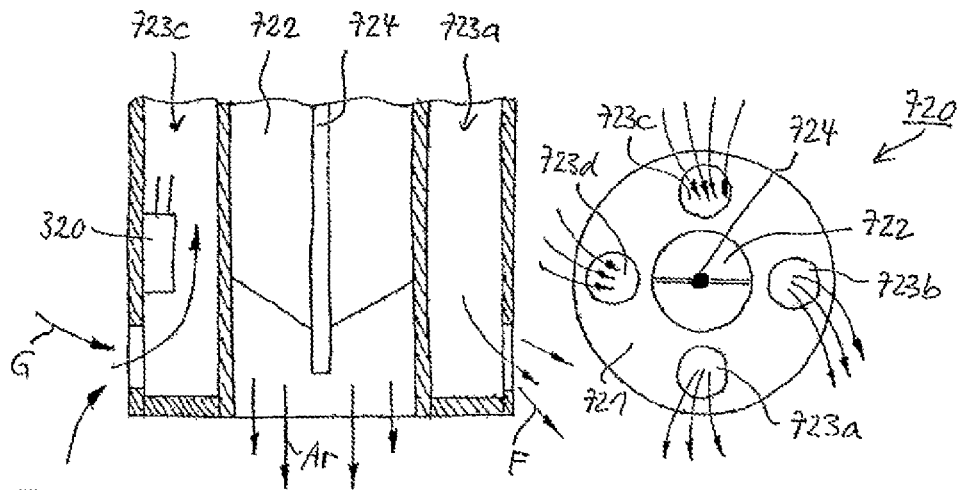
Figure 2C:
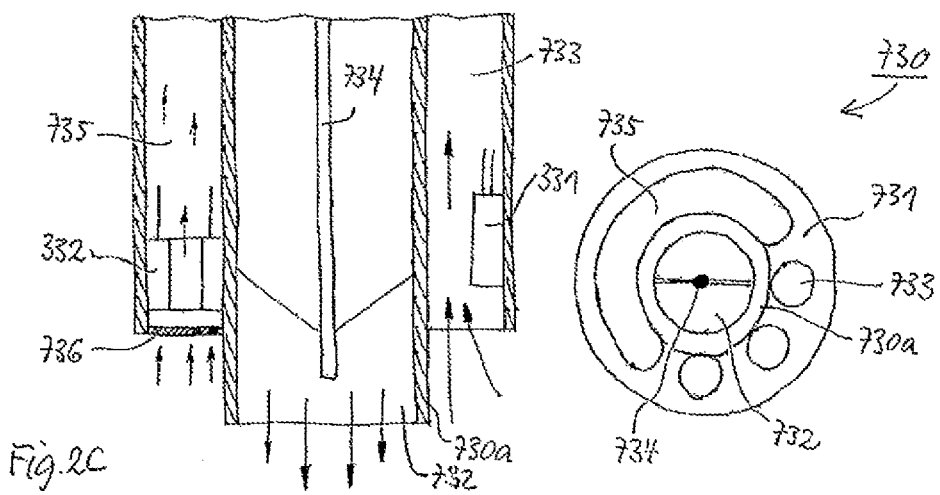
Figure 2D:
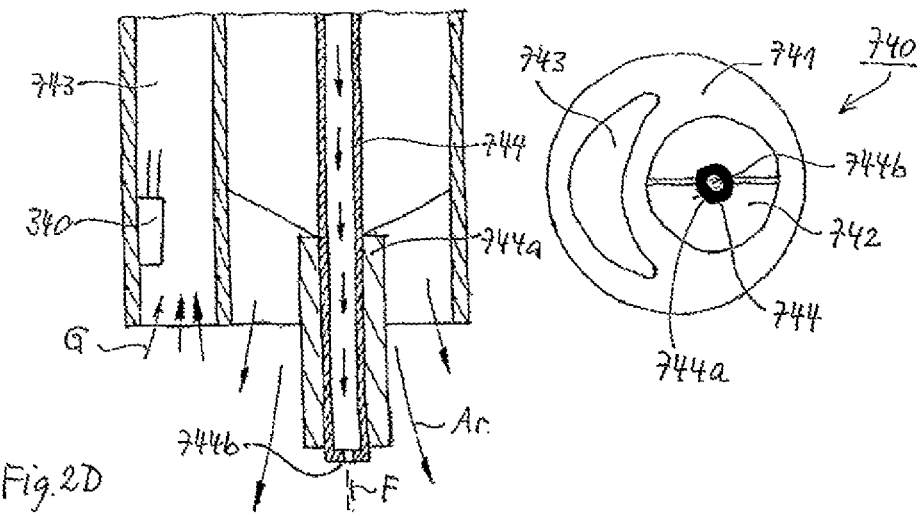
Figure 3A:
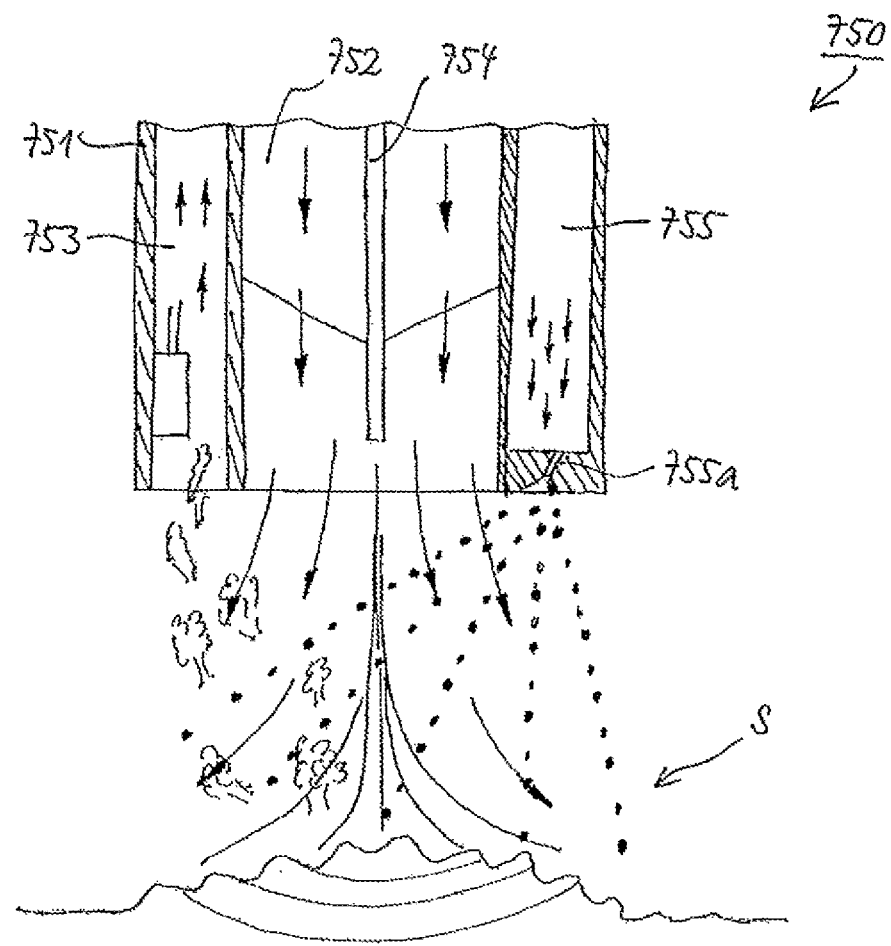
Figure 3B:
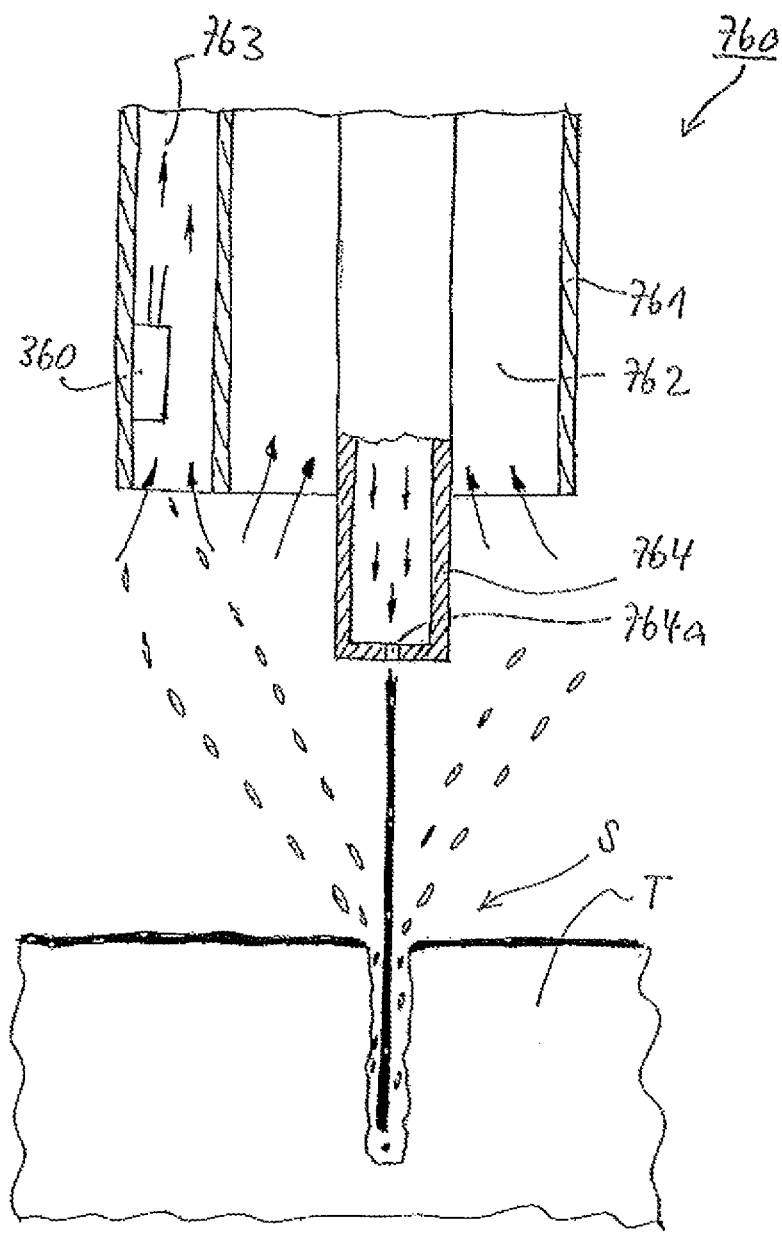
Figure 4A:
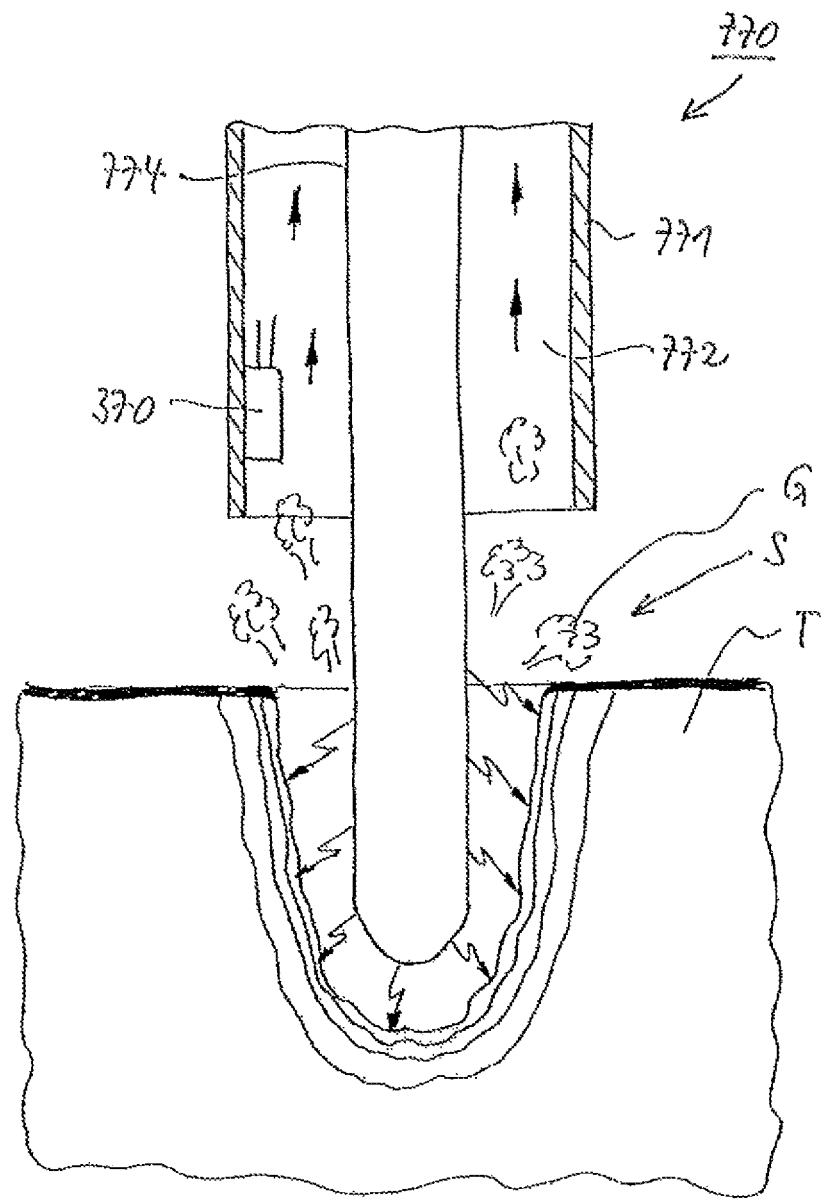
Figure 4B:
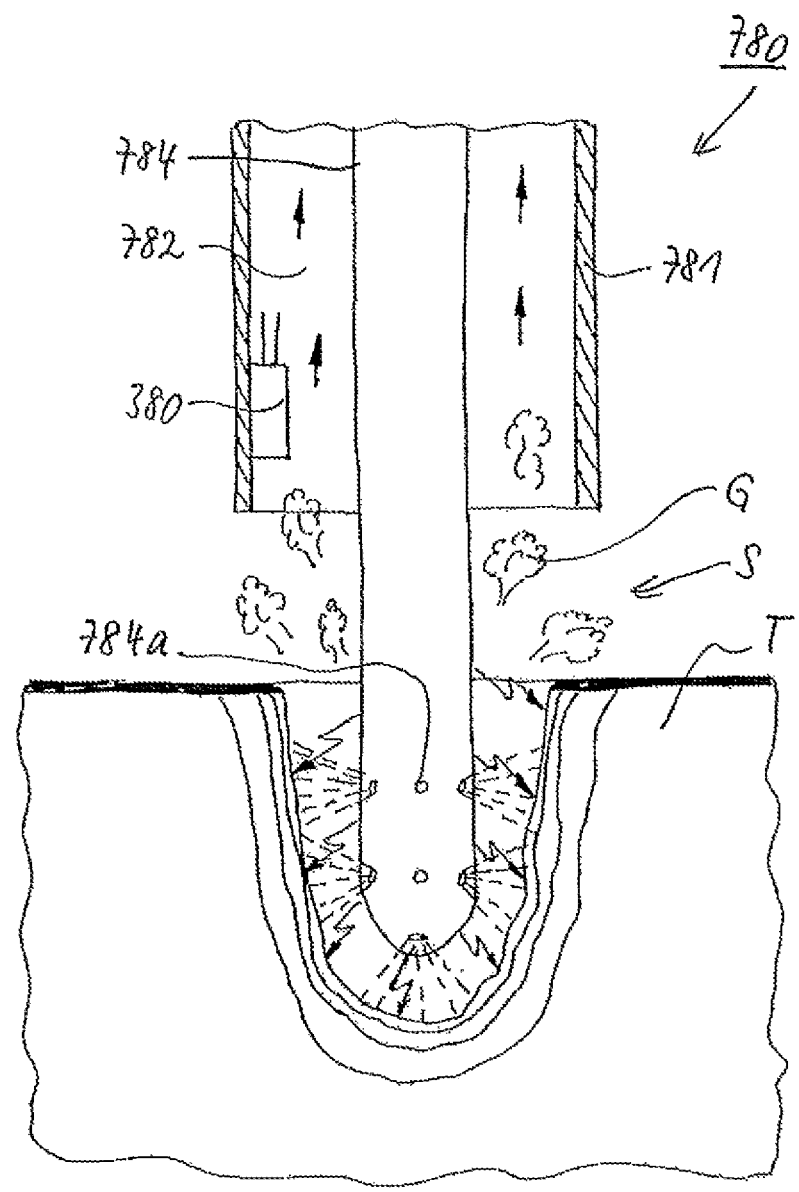
Figure 4C:
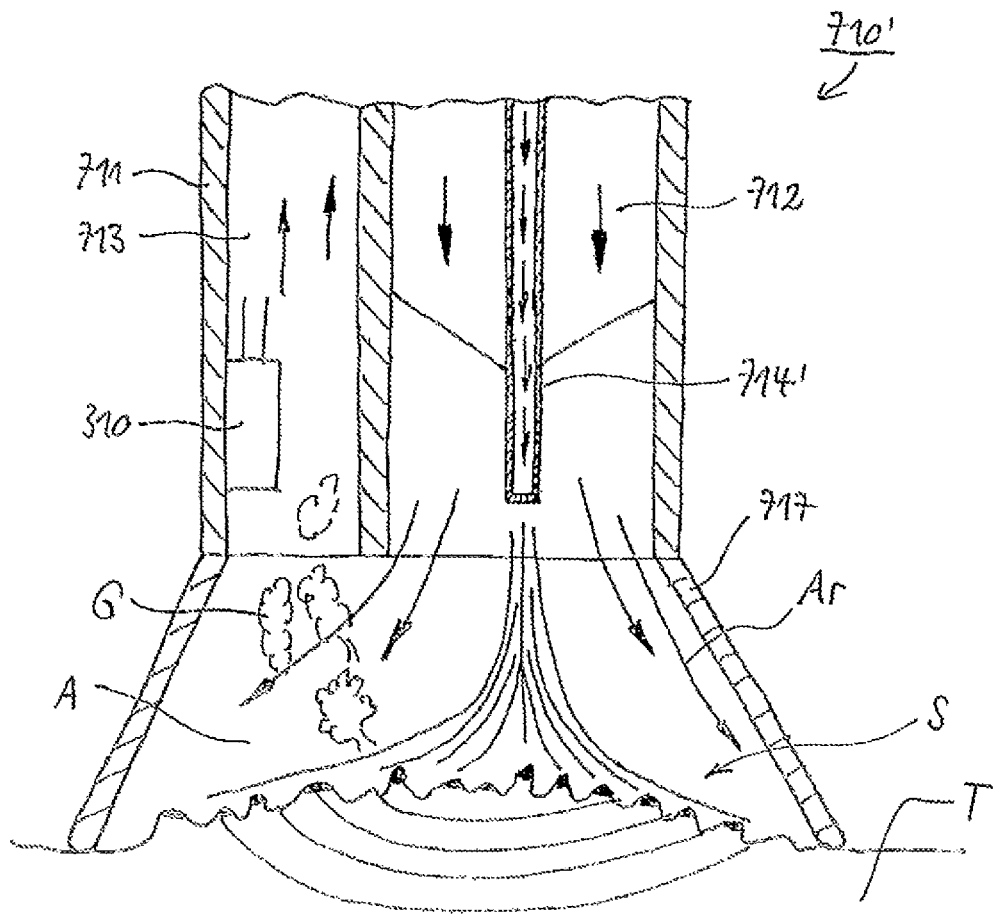
Figure 4D:
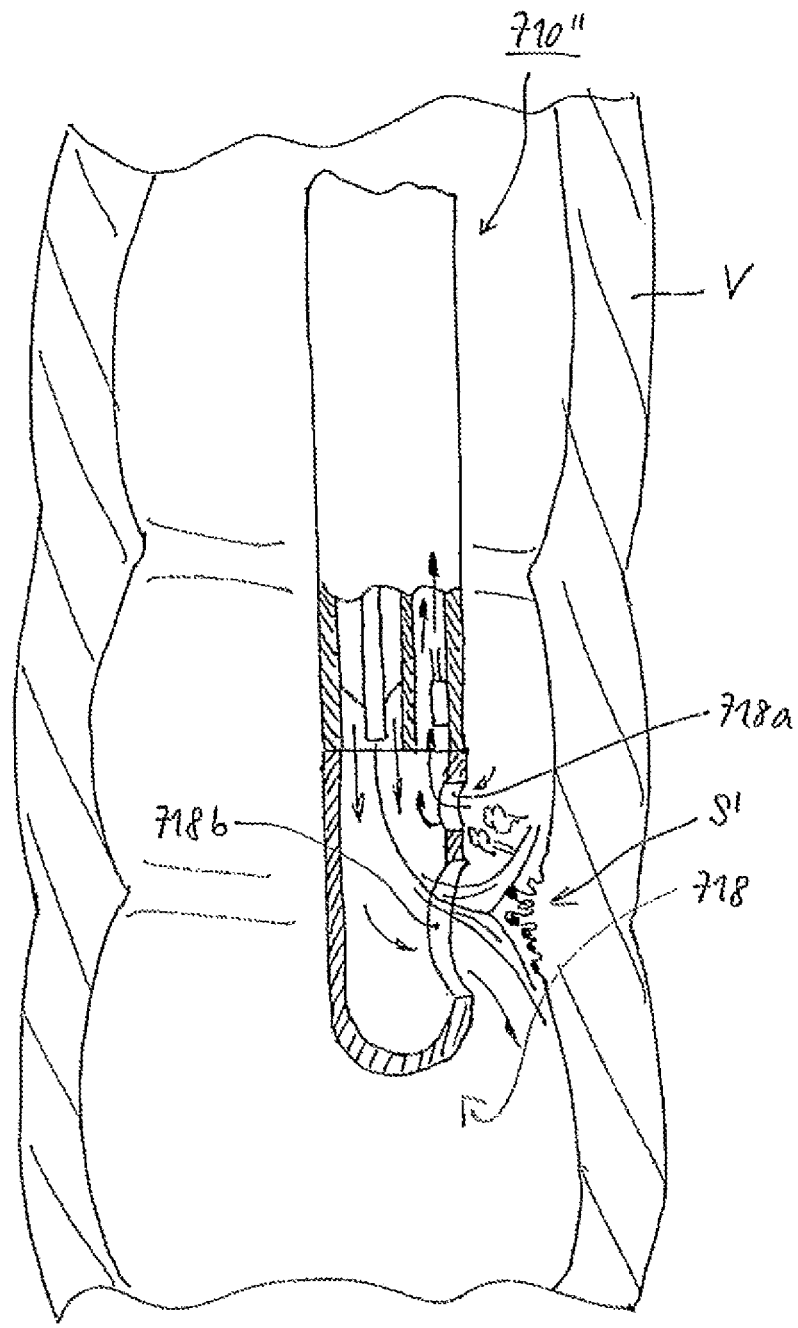
Figure 5A:
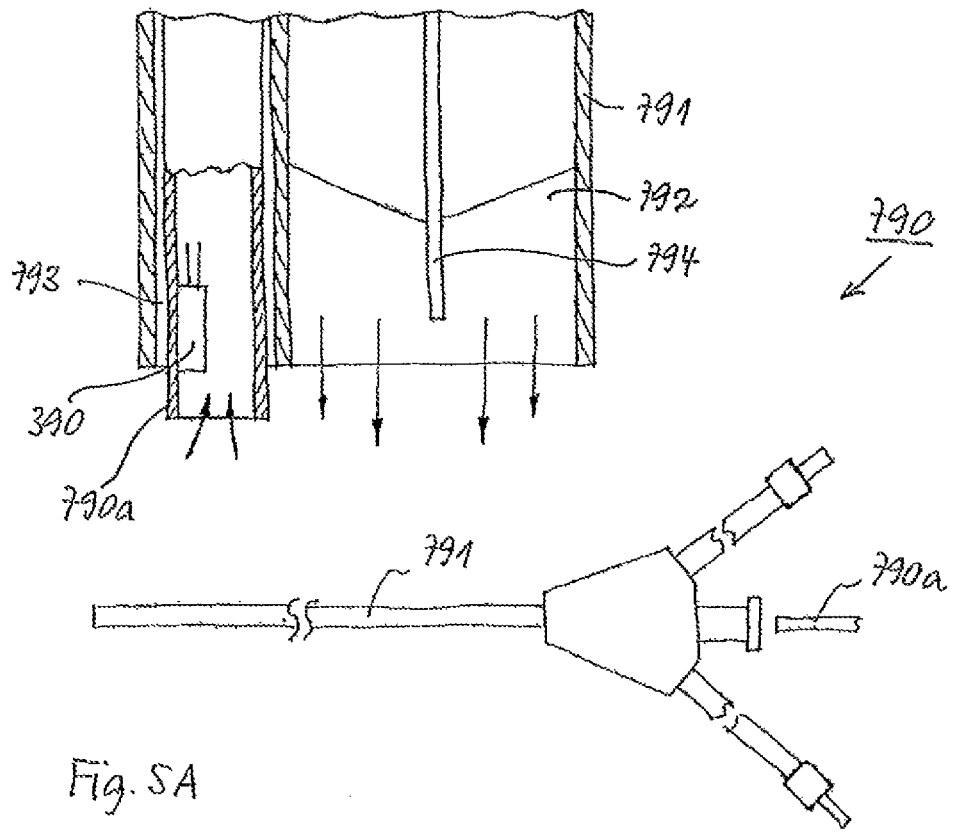
Figure 5B:
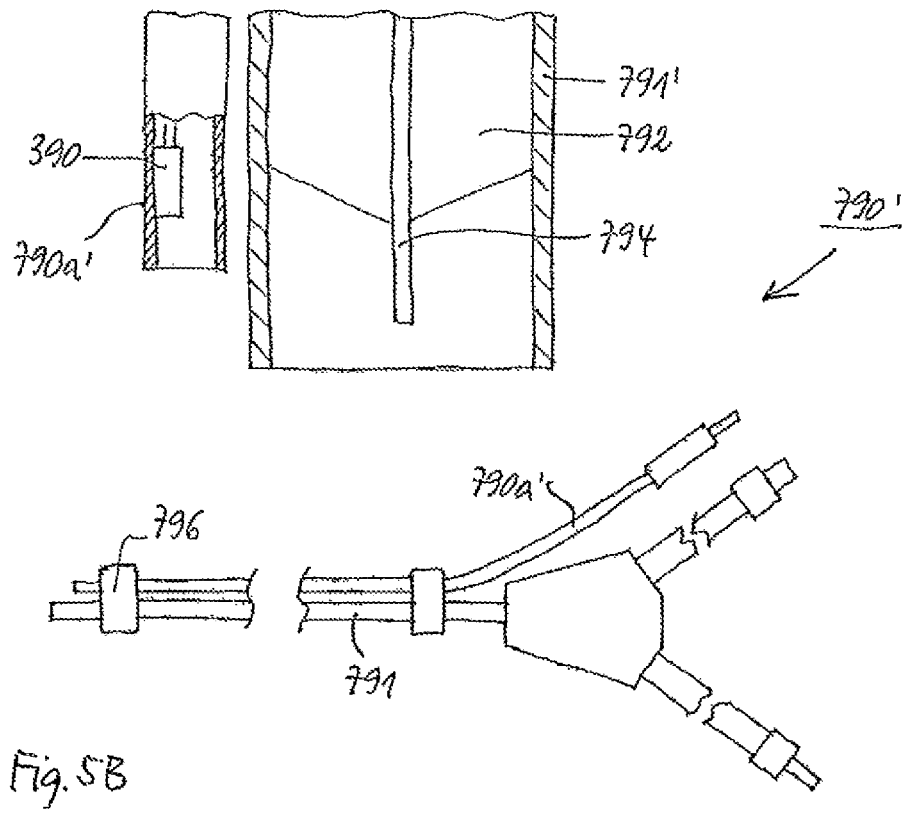
Figure 6:
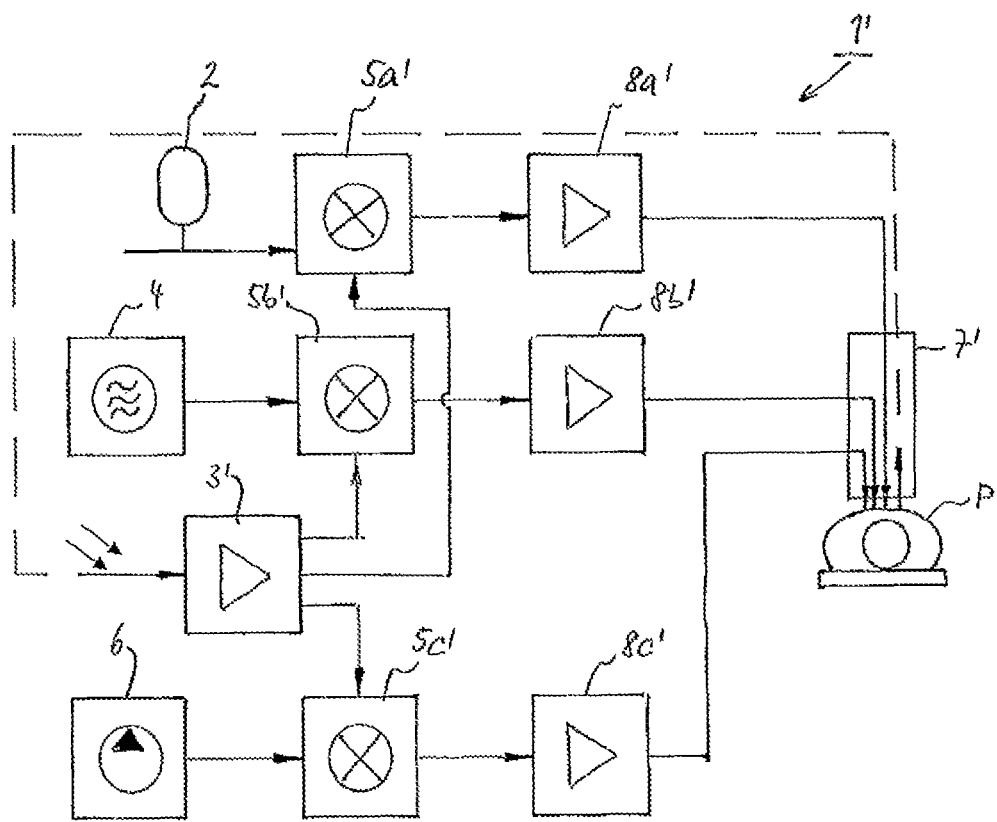
Figure 7A:
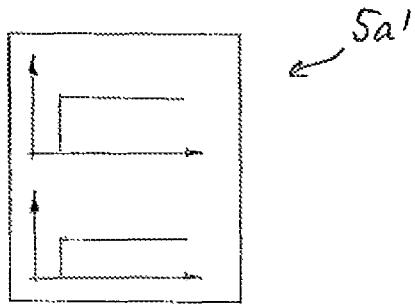
Figure 7B:
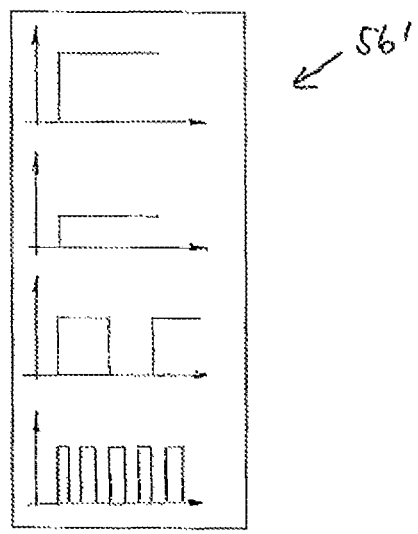
Figure 7C:
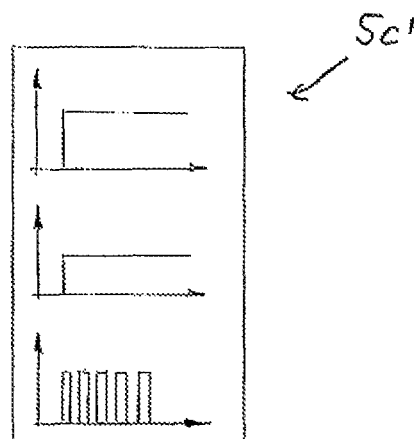
Figure 8A:
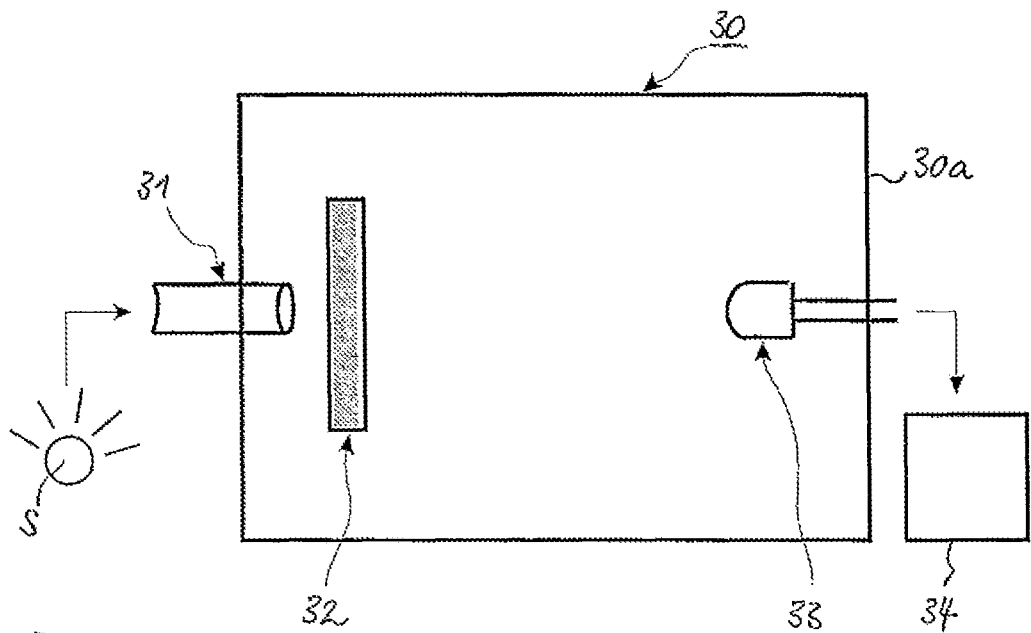
Figure 8B:
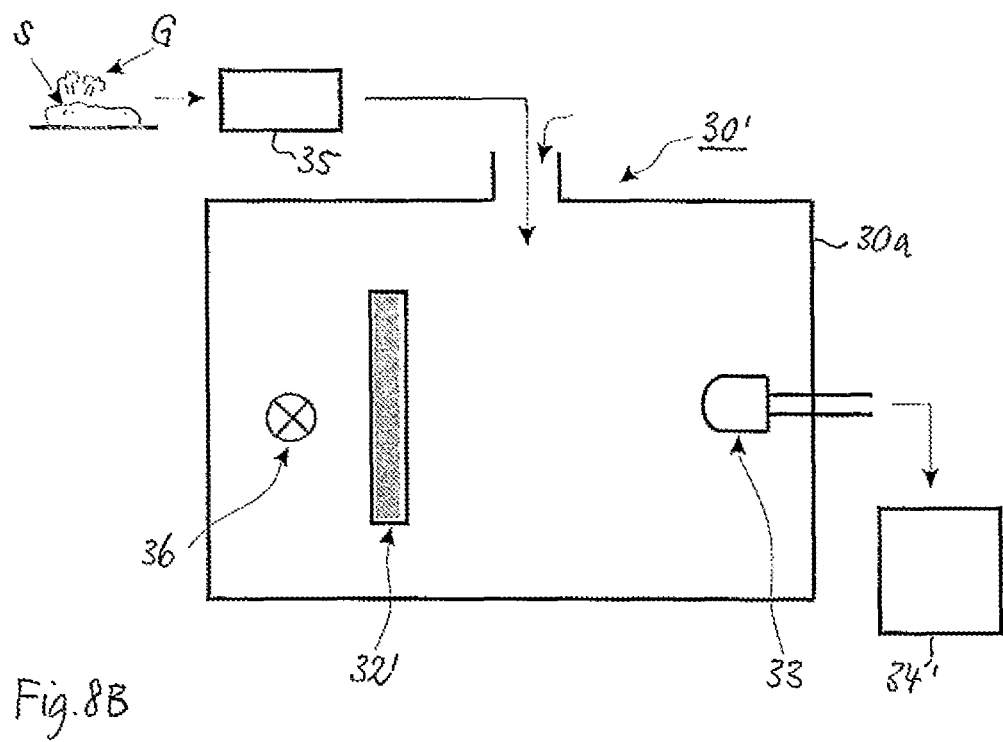

Advantages and expedient aspects of the invention otherwise emerge from the following description of preferred exemplary embodiments on the basis of the figures, in which:

FIG. 1 shows a schematic overall view of an electrosurgical assembly according to the invention, FIGS. 2A-2D show exemplary embodiments of an electrosurgical instrument as a component of such an assembly in views of details, in each case in a longitudinal sectional representation of the distal end and a distal plan view, FIGS. 3A and 3B show further embodiments of the electrosurgical instrument in views of details, in each case as a longitudinal sectional representation of the distal end in an application situation at a treatment site, FIGS. 4A-4D show further embodiments of the electrosurgical instrument in views of details, in each case as a longitudinal sectional representation of the distal end in an application situation at a treatment site, FIGS. 5A and 5B respectively show a plan view and a view of a detail (longitudinal section of the distal end) of further embodiments of the electrosurgical instrument, FIG. 6 shows a functional block diagram of an embodiment of the electrosurgical assembly, FIGS. 7A-7C show pulse diagrams for illustrating refinements of the operating mode of a treatment unit according to the invention and FIGS. 8A and 8B show schematic representations of evaluation devices by way of example of an electrosurgical assembly according to the invention.

FIG. 1 schematically shows an electrosurgical assembly 1 in use at a treatment site S on biological tissue T, a heat input H into the tissue being brought about by the exposure to a treatment energy E and emissions, in particular fumes G, being given off from the treatment site S into the atmosphere A located above it. The emissions are detected by means of a detection device 3, and the output signal thereof is fed to a treatment unit 5, which for its part is connected on the output side to an electrosurgical instrument 7, by way of which the treatment process is performed in a way that is controlled by the treatment unit and, in particular, the treatment energy E is emitted.

FIG. 2A shows in detail the distal end of an instrument 710 in use at a treatment site S. Two lumina 712, 713 are formed in an instrument body 711, and in the smaller lumen 713, through which the fumes G are extracted from the atmosphere A above the treatment site, there is fitted a fume detector 310. A noble gas, for example argon, for flushing around a centrally arranged RF electrode 714 and for influencing the treatment process at the treatment site S is supplied by way of the larger lumen 712.

FIGS. 2B-2D show modifications of the structural design of the instrument as shown in FIG. 2A, parts that correspond functionally to one another being designated by similar reference signs as in FIG. 2A and not explained again below.

The structure of the instrument 720 as shown in FIG. 2B differs from that of the instrument 710 firstly by a centric placement of the larger lumen 722 in relation to the supply of the noble gas, the RF electrode 724 in turn being placed concentrically in the lumen 722. Four smaller lumina 723a-723d are arranged in a uniformly distributed manner around the lumen 722. Of these, the two lumina 723c and 723d serve for the extraction of gases G from the treatment area and for the detection thereof by means of a gas detector 320, while the two remaining outer lumina 723a and 723b supply further fluids F (gases or liquids, apart from the noble gas supplied by way of the central lumen) to the treatment site. As can be seen from the left part of the figure, the distal orifices of the outer lumina are not located in the end face of the instrument but in the lateral region thereof. It is also clear from this that the right part of this figure is not a plan view of the distal end of the instrument, but a cross-sectional representation obtained near the distal end.

FIG. 2C shows as a further modification an instrument 730, which is distinguished from the previously described instruments 710 and 720 firstly by a graduated distal end with a projecting middle region 730a. Also provided here are a number of identical smaller lumina 733 with a circular cross section and a larger lumen 735, partially surrounding the middle region 730a of the instrument in a C-shaped manner, in which there are fitted various detectors 331 and 332 for detecting various constituents of the gases G and/or further parameters of the atmosphere above the treatment site. The C-shaped lumen 735 is in this case closed in the distal direction by a semipermeable membrane 736 to protect the detector 332 arranged there from rising vapor or moisture at the treatment site.

FIG. 2D shows as a further modification an instrument 740, which, like the aforementioned embodiments, has a large lumen 742 for supplying the RF energy and treatment fluids. Apart from this, in the instrument body 741 there is only formed a single further lumen 743, which here has a sickle shape and in which—in a way similar to in the case of the first embodiment as shown in FIG. 2A—there is placed a single detector 340 for analyzing the gases G.

A major modification with respect to the instrument 710 is that the RF electrode 744 is formed here as a metal tube, through which a treatment fluid, in particular gaseous oxygen or an NaCl solution, can be passed to the treatment site. Moreover, the electrode 744 is embodied here as projecting distally beyond the end of the instrument and has in its end region a thermally resistant enclosure 744a of an electrical insulator, in order to avoid (additional) carbonization caused by strong arcs in an APC application. Materials that come into consideration for the covering 744a are ceramics or else high-temperature-resistant plastics, for instance PTFE-based plastics. A nozzle 744c in the end face of the electrode tube 744 provides for an atomizing of a supplied liquid above the treatment site.

FIG. 3A shows as a further embodiment an instrument 750 in use at a treatment site S, which in turn has a number of lumina 725, 753 and 755. With regard to the structure and the function of the lumina 752, 753 and the RF electrode 754 arranged in the lumen 752, the instrument 750 corresponds to the instrument 710 as shown in FIG. 2A and described further above. A device for supplying and discharging a treatment fluid selectively, and possibly in a spraying manner, such as, for instance, a physiologically effective aqueous solution and/or an oxidizing agent, with the lumen 755 and the distal opening 755a thereof extending obliquely and widening outwardly, is added. The inclination and shape of the opening 755a are dimensioned such that the treatment fluid is discharged under a suitable pressure and in a concentrated manner above the treatment site S.

FIG. 3B shows, as a modification of the instrument 740 as shown in FIG. 2D and described further above, in a schematic representation a multi-lumen water-jet applicator 760 with an inner active RF electrode 764, which is formed as a metal tube, through which liquid flows out at a high flow rate through a nozzle opening 764a, in order to achieve the desired effect in the tissue. Introduced liquid and blood is extracted into the extraction channel 762 when the probe is placed onto the tissue. By way of a further channel 763, substances, for example, aerosols, are extracted parallel to the application by negative pressure through the instrument past a sensor 360, which is attached to the distal end of the instrument, and are analyzed.

FIG. 4A shows a schematic representation of a monopolar RF instrument 770 for cutting biological tissue, in which the active electrode 774 is encased by a tube 761, by way of which the corresponding fume G can be extracted. In the tube, which may be provided centrally or parallel to the axis of the active electrode, there is located at the distal end a sensor 370 for the fume analysis.

FIG. 4B shows a schematic representation of a further monopolar RF instrument 780 for cutting biological tissue, in which the active electrode 784 has at the tip small openings 784a, by way of which liquid or gaseous substances can leave, and which is formed such that the fumes G or aerosols can be extracted by way of an extraction tube 782 and can be analyzed by way of a sensor 380.

FIG. 4C shows the use of an instrument 710' that is modified somewhat with respect to the embodiment as shown in FIG. 2A. One way in which this instrument differs from the instrument 710 is by a hollow embodiment of the electrode 714', inside which a treatment fluid is supplied to the treatment site S, and another way is by the distal provision of a conically widening attachment 717, which largely separates the atmosphere A above the treatment site S from the remaining atmosphere. This attachment 717 consequently avoids with a high degree of reliability the escape of fumes into the operating room and also makes more efficient use of the supplied treatment fluids possible.

FIG. 4D diagrammatically shows the use of an instrument 710" at a treatment site S' in a hollow organ V (for example the intestine) of a patient. The particular structural refinement of this instrument 710" is that of a distally fitted cap 718 with two lateral openings 718a, 718b, by way of which the fumes are extracted into the interior of the instrument and treatment fluids are supplied from the instrument to the treatment site S'. Otherwise, the structure corresponds to that of the previously described instrument 710' or of the instrument 710 explained further above, and to this extent is not described again.

FIG. 5 shows an APC instrument 790, the instrument body of which in turn is constructed in a way similar to in the case of the instruments described further above, so that the reference signs for the individual parts or regions are based on FIGS. 2A-3B. The instrument 790 has the greatest similarity with the instrument 710 as shown in FIG. 2A; a major difference with respect to the latter is in the provision of a separate measuring probe 790a, which is arranged displaceably in a proximal-distal manner in the lumen 793 and can consequently bring the detector 390 fitted therein particularly close to a treatment site.

FIG. 5B shows as a modification of the last-mentioned embodiment, a further APC instrument 790', in which a displaceable measuring probe 790a' with the detector 390 is provided displaceably on the outside of a modified (single-lumen) instrument body 791'. Serving for securing the probe 790a' on the main body 791' of the instrument are attachment clips 796, in which the probe can slide.

FIG. 6 schematically shows in the form of a functional block diagram an electrosurgical assembly 1' with a surgical instrument 7', the basic structure and use of which correspond to the assembly that is shown in FIG. 1 and which is used on a patient P. An emission sensor 3' with an assigned measuring amplifier performs a predetermined detection process at the treatment site, for instance a fume analysis, a sensing of CO, a temperature sensing or else a sensing of the distance between the end of the instrument and the tissue, etc., and, with the aim of suitably influencing the treatment process, its output signal is fed to various control devices. Here, these are a flow control device 5a' for the gas stream of a treatment gas supplied from a gas cylinder 2, an RF control device 5b' for controlling the treatment energy provided by an RF generator 4 and a flushing liquid control device 5c' for the flow control of a flushing liquid provided from a source 6. It is also schematically represented in the figure that additional amplifier or control devices 8a', 8b' and 8c' may be provided in all of the "channels" for influencing the treatment process.

FIGS. 7A-7C show by way of example in the manner of pulse diagrams possibilities for the modulation of the treatment gas stream by the first control device 5a' (FIG. 7A), of the RF generator power output by the second control device 5b' (FIG. 7B) and of the provision of flushing liquid by the third control device 5c' (FIG. 7C).

FIG. 8A shows a basic diagram of a sensor system 30, in which the light emission at the treatment site S (in the visible or ultraviolet wavelength range) is coupled into an optical waveguide 31. This polychromatic light emission is filtered with the aid of an optical filter 32 in such a way that only one wavelength or a narrow band of wavelengths that is characteristic of the process to be observed (for example the process of carbonizing the tissue surface) is allowed through. This wavelength or this band of wavelengths is detected by a suitable photodiode 33 and converted into a voltage signal, the voltage signal being proportional to the intensity of the filtered wavelength or band of wavelengths. This voltage signal is evaluated by an evaluation unit 34 and used for controlling/regulating the RF generator and the additive supply.

FIG. 8B shows a basic diagram of a further sensor system 30', in which the fume occurring in an electrosurgical application is introduced by means of a pump 35 into the sensor housing 30a through a hose line (not shown). In the sensor housing there is a polychromatic or monochromatic light source 36, an optical filter 32' and a photodiode 33. The optical filter filters an optical wavelength or a band of wavelengths out of the polychromatic spectrum of the light source. (It may be omitted if a monochromatic light source is used). The radiation leaving the filter impinges on molecules of the fume G and is completely or partially absorbed by them. The remaining radiation intensity impinges on the photodiode, which generates a voltage signal in dependence on the incident radiation intensity. This voltage signal is evaluated by an evaluation unit 34' and used for controlling/regulating the RF generator and the additive supply.

The embodiment of the invention is not restricted to the examples described above and aspects highlighted, but is similarly possible in many modifications that are within the capabilities of a person skilled in the art.

The invention claimed is:

1. An electrosurgical assembly with an electrosurgical instrument, a detection device for detecting a predetermined gaseous constituent of the atmosphere in the region of a treatment site, which device has a sensor for sensing an optical variable at the treatment site, and a treatment unit, which can be connected to the instrument and has a power generator for providing RF energy, wherein the treatment unit is configured for influencing the treatment process in dependence on an output signal of the detection device are provided in the treatment unit, wherein at least part of the detection device is arranged in a proximal region of the electrosurgical instrument and the instrument has a first fluid channel for passing gas through to the detection device, and treatment unit has a fluid source for providing a treatment fluid suitable for influencing the treatment process, in particular an oxygen or noble-gas cylinder or a water tank for receiving water or an aqueous solution, and the electrosurgical instrument has a second fluid channel for passing the treatment fluid for influencing the treatment process through to the distal end of the instrument.

2. The electrosurgical assembly as claimed in claim 1, wherein the detection device has an analysis device for analyzing aerosol or solid particles transported with the gas.

3. The electrosurgical assembly as claimed in claim 1, further comprising a first conveying device for conveying gas in the distal-proximal direction and/or a second conveying device for conveying a treatment fluid for influencing the treatment process in the proximal-distal direction is/are provided in the electrosurgical instrument or in fluid connection with it.

4. The electrosurgical assembly as claimed in claim 1, further comprising a flow controller for controlling the amount of treatment fluid suitable for influencing the treatment process that is supplied to the treatment site per unit of time.

5. The electrosurgical assembly as claimed in claim 1, wherein the electrosurgical instrument has at or near the distal end a plurality of openings connected to the second fluid channel for the spatially distributed outletting of the treatment fluid.

6. The electrosurgical assembly as claimed in claim 1, wherein the second fluid channel is arranged within an electrosurgical electrode of the instrument.

7. The electrosurgical assembly as claimed in claim 1, wherein the treatment unit has a control device of the power generator that is connected in signaling terms to the output of the detection device, in particular an on/off control and/or power output control.

* * * * *

UNITED STATES PATENT AND TRADEMARK OFFICE
CERTIFICATE OF CORRECTION

| | |
|---|---|
| PATENT NO. | : 9,216,051 B2 |
| APPLICATION NO. | : 13/576246 |
| DATED | : December 22, 2015 |
| INVENTOR(S) | : Klaus Fischer et al. |

It is certified that error appears in the above-identified patent and that said Letters Patent is hereby corrected as shown below:

On the title page item (75), line 5, Inventors, update the address of inventor, Mara Szyrach, as follows:

Replace "Tuebingen (DE)" with --Zuerich (CH)--.

Signed and Sealed this
Seventeenth Day of May, 2016

Michelle K. Lee
*Director of the United States Patent and Trademark Office*